United States Patent
Shim et al.

(10) Patent No.: US 8,080,036 B2
(45) Date of Patent: Dec. 20, 2011

(54) PEDICLE SCREW

(75) Inventors: Young Bock Shim, Seoul (KR); Ju Woong Jang, Seoul (KR); Dae Kwan Kim, Gyeonggi-do (KR); Sok Kyun Hong, Seoul (KR)

(73) Assignee: Korea Bone Bank, Inc., Seoul (KR)

(*) Notice: Subject to any disclaimer, the term of this patent is extended or adjusted under 35 U.S.C. 154(b) by 388 days.

(21) Appl. No.: 12/359,103

(22) Filed: Jan. 23, 2009

(65) Prior Publication Data

US 2010/0094353 A1     Apr. 15, 2010

(30) Foreign Application Priority Data

Oct. 9, 2008  (KR) ................. 10-2008-0099291

(51) Int. Cl.
*A61B 17/70* (2006.01)
(52) U.S. Cl. ........................ 606/246; 606/264
(58) Field of Classification Search .............. 606/246, 606/250, 260, 264, 265, 270, 278, 289
See application file for complete search history.

(56) References Cited

U.S. PATENT DOCUMENTS

| 5,474,555 | A | 12/1995 | Puno | |
|---|---|---|---|---|
| 7,232,190 | B2* | 6/2007 | Fraisse et al. | 303/11 |
| 2003/0100896 | A1* | 5/2003 | Biedermann et al. | 606/61 |
| 2005/0038438 | A1* | 2/2005 | Anderson et al. | 606/73 |
| 2008/0009862 | A1* | 1/2008 | Hoffman | 606/61 |
| 2008/0305145 | A1 | 12/2008 | Shelby | |

* cited by examiner

*Primary Examiner* — Brian Pellegrino
*Assistant Examiner* — Matthew Schall
(74) *Attorney, Agent, or Firm* — Christensen O'Connor Johnson Kindness PLLC

(57) ABSTRACT

A pedicle screw is provided to be inserted into and fixed to a pedicle of a spinal disease patient, and more particularly, a pedicle screw in which a screw thread of a clamp screw is formed to have dents and protrusions with trapezoid cross-sections so as to form a predetermined gap with a screw thread of a fixing unit having dents and protrusions with rectangular cross-sections when the clamp screw is combined with the fixing unit, and the screw thread of the clamp screw has different pitches to disperse an external impact so as to further firmly combine the clamp screw with the fixing unit.

10 Claims, 7 Drawing Sheets

PEDICLE SCREW

BACKGROUND

The present invention relates to a pedicle screw which is inserted into and fixed to a pedicle of a spinal disease patient, and more particularly, to a pedicle screw in which a screw thread of a clamp screw is formed to have dents and protrusions with trapezoid cross-sections so as to form a predetermined gap with a screw thread of a fixing unit having dents and protrusions with rectangular cross-sections when the clamp screw is combined with the fixing unit, and the screw thread of the clamp screw has different pitches to disperse an external impact so as to further firmly combine the clamp screw with the fixing unit.

In general, spinal diseases refer to representative symptoms in which nerves protruding from left and right sides of each of bones are pressed by damaged disks to cause spinal disease patients pains.

A patient having a spine of which part has been damaged is not able to smoothly do personal activities. Even when the damage to the part of the spine is not serious, the damaged part of the spine is pressed by or contacts another adjacent part to cause the patient pains. Therefore, an operation is to be performed with respect to a patient having a spine of which part is broken down or damaged using an artificial aid in order to support the damaged part.

A spinal artificial aid mainly used in this case includes a pedicle screw and a spinal rod so as to assist a damaged spine in restoring to its normal state, wherein the pedicle screw is inserted onto upper and lower parts of the damaged spine so as to operate as a fixing bar and the spinal road is connected to the damaged spine through the pedicle screw so as to operate as a support bar.

Since a patient lives with semi-permanently implanted with an artificial aid, the artificial aid inserted into the body of the patient is not to be deformed or loosened by longtime activities of the patient.

In other words, the pedicle screw is to be firmly combined with the spinal rod in order to maintain the artificial aid in the body of the patient. Various researches and developments have been conducted in order to solve this.

Figure 1:
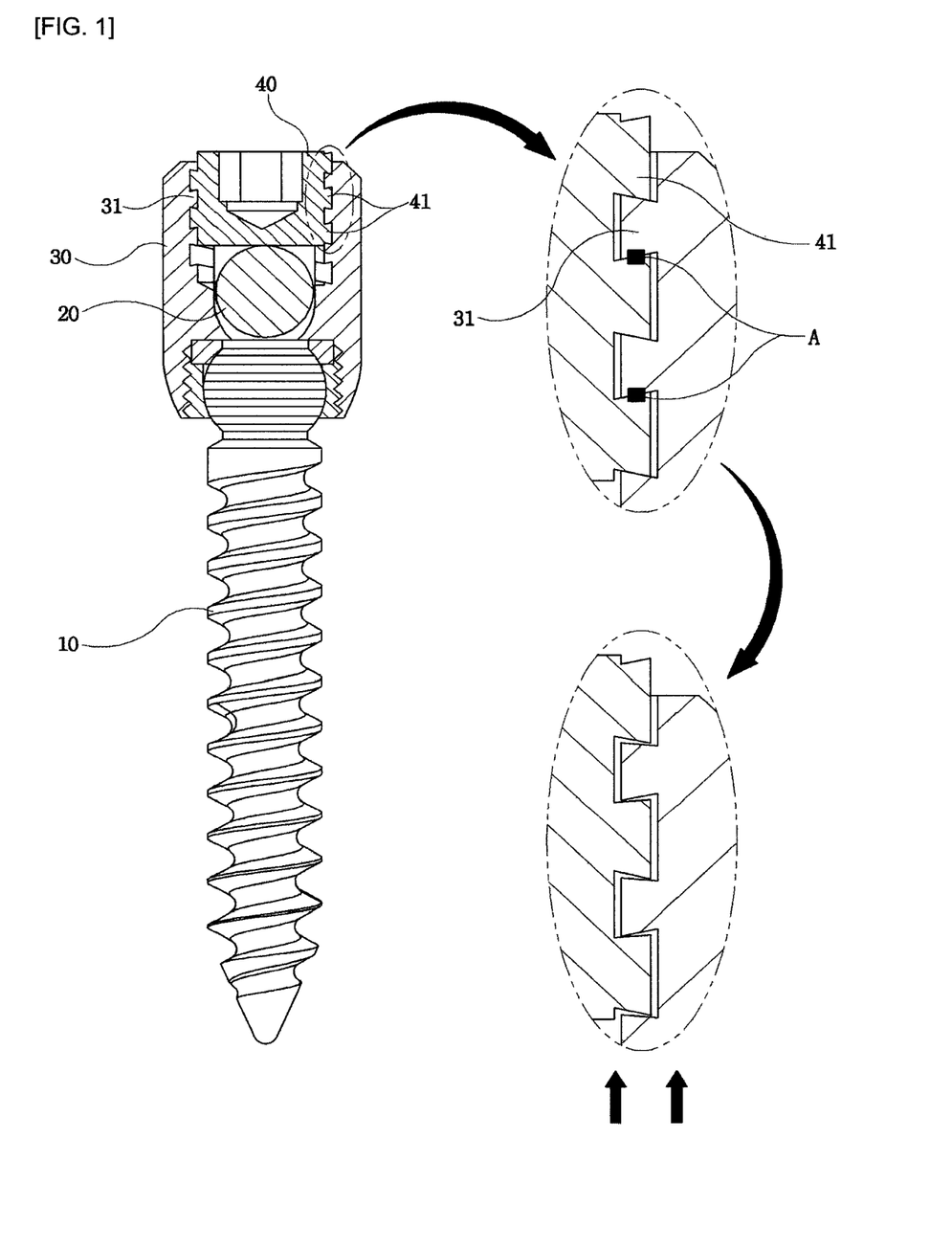
FIG. 1 is a cross-sectional view of a conventional pedicle screw.

FIG. 1 is a cross-sectional view of a conventional pedicle screw. Referring to FIG. 1, the conventional pedicle screw includes a screw bar 10, a spinal rod 20, and a head 30. The head 30 includes a U-shaped groove which is connected to the screw bar 10 so as to house the spinal rod 20. A fixing screw thread 31 is formed at an inner surface of the U-shaped groove of the head 30 to be tapered, so that dents of the fixing screw thread 31 decrease toward the center of the head 30.

The pedicle screw further includes a clamp screw 40 which is combined with the head 30. Here, a clamp screw thread 41 is formed at an outer surface of the clamp screw 40 to correspond to the fixing screw thread 31 formed at the inner surface of the U-shaped groove of the head 30. Thus, the clamp screw 40 is fixed into the head 30 through the clamp screw thread 41.

However, when the spinal rod 20 continuously receives load from a movement of a patient, the spinal rod 20 pushes the clamp screw 40 and thus separate from the clamp screw 40. In this case, the clamp screw thread 41 of the clamp screw 40 is firmly tightened to the fixing screw thread 31 of the head 30. Thus, the load is concentrated on positions "A," and thus the clamp screw thread 41 of the clamp screw 40 is bent so as to push the fixing screw thread 31 of the head 30. As a result, the head 30 becomes apart from the clamp screw 40, which loosens the combination between the head 30 and the clamp screw 40.

Also, the fixing screw thread 31 of the head 30 and the clamp screw thread 41 of the clamp screw 40 receive the load through their surfaces onto which the load is applied. Thus, the fixing screw thread 31 and the clamp screw thread 41 absorb the load not disperse the load. As a result, the combination between the fixing screw thread 31 and the clamp screw thread 41 is further easily loosened.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The described embodiments are directed to a pedicle screw in which a fixing screw thread is formed at an inner surface of a U-shaped housing groove formed in a fixing unit so as to have dents and protrusions with rectangular cross-sections, wherein the dents have rounded corners, a clamp screw thread is formed at an outer surface of a clamp screw combined with the fixing unit so as to have dents and protrusions with right-angled trapezoid cross-sections, and pitches of the clamp screw thread of the clamp screw are different from one another to disperse external load, in order to further firmly combine the clamp screw with the fixing unit so as to prevent a spinal rod from being apart from the fixing unit.

According to an aspect of an embodiment, there is provided a pedicle screw including: a fixing unit which includes a U-shaped housing groove which is formed in a side of the fixing unit to be opened upward so as to house a spinal rod, a fixing screw thread which is formed at an inner surface of the U-shaped housing groove so as to have dents and protrusions with rectangular cross-sections, and a combination groove which is formed in a lower surface of the fixing unit so as to penetrate the lower surface of the fixing unit; a screw bar which includes a spherical joint which constitutes an upper part of the screw bar and a screw thread which is formed at an outer surface of the screw bar to be inserted into a pedicle through the combination groove of the fixing unit; and a clamp screw which includes a clamp screw thread which is formed at an outer surface of the clamp screw to have dents and protrusions with right-angled trapezoid cross-sections so as to form a predetermined gap with the fixing screw thread of the fixing unit when the clamp screw is combined with the fixing unit.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

While illustrative embodiments have been illustrated and described, it will be appreciated that various changes can be made therein without departing from the spirit and scope of the invention.

Figure 2:
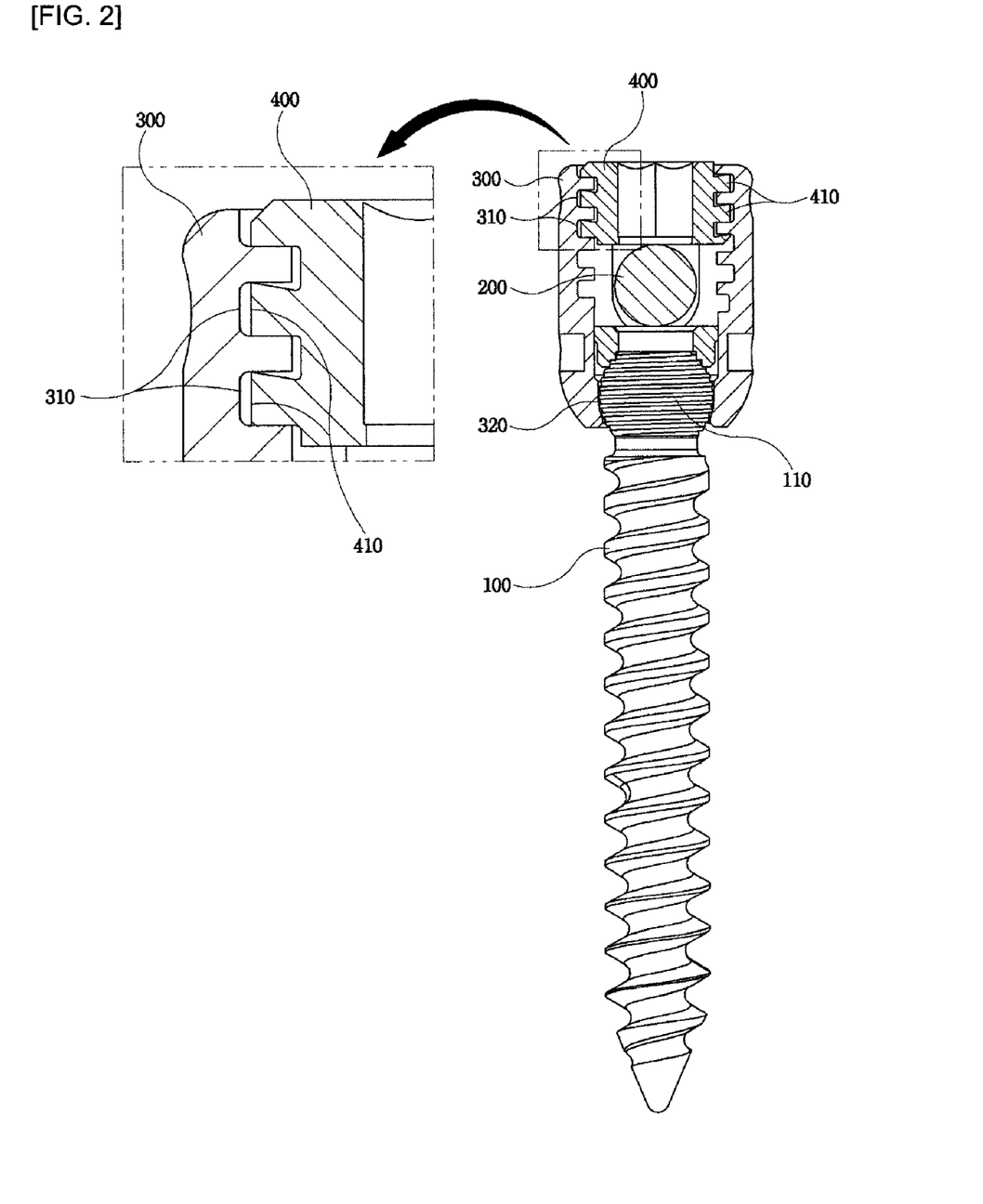
FIG. 2 is a cross-sectional view of a pedicle screw according to an embodiment of the present invention.

FIG. 2 is a cross-sectional view of a pedicle screw according to an embodiment of the present invention. Referring to FIG. 2, the pedicle screw of the present embodiment includes a fixing unit 300, a screw bar 100, and a clamp screw 400. The fixing unit 300 includes a U-shaped housing groove 330 which is formed in a side of the fixing unit 300 so as to be opened upward and a combination groove 320 which is formed in a lower surface of the fixing unit 300 so as to penetrate the lower surface of the fixing unit 300. The screw bar 100 includes a spherical joint 110 which constitutes an upper part of the screw bar 100 and a screw thread which is formed at an outer surface of the screw bar 100, so as to be inserted into the pedicle screw through the combination groove 320 of the fixing unit 300. The clamp screw 400 includes a clamp screw thread 410 which is formed at an outer surface of the clamp screw 400 so as to be combined with the fixing unit 300.

The U-shaped housing groove 330 is formed in the fixing unit 300 to be opened upward so as to house a spinal rod 200. A fixing screw thread 310 is formed at an inner surface of the U-shaped housing groove 330 so as to have dents and protrusions with rectangular cross-sections, wherein the dents have rounded corners.

The combination groove 320 is formed in the lower surface of the fixing unit 300 to house the screw bar 100 so as to be combined with the screw bar 100. A tapered screw thread is formed at an inner surface of the combination groove 320.

The screw thread is formed at the outer surface of the screw bar 100, and the spherical joint 110 is formed at the upper part of the screw thread 100 to form a single body with the screw bar 100. Thus, the spherical joint 110 is inserted into the combination groove 320 so as to connect the screw bar 100 to the fixing unit 300 through the combination groove 320.

Here, the screw bar 100 includes the spherical joint 110 so as to move inside the fixing unit 300. Alternatively, the screw bar 100 may be combined with the fixing unit 300 to form a single body without separating from the fixing unit 300, i.e., may be realized in various forms.

The clamp screw thread 410 is formed at the outer surface of the clamp screw 400 so as to engage with the fixing screw thread 310 formed at the inner surface of the U-shaped housing groove 330 of the fixing unit 300. The clamp screw 400 is inserted into and combined with the fixing unit 300 through the engagement of the clamp screw thread 410 with the fixing screw thread 310 so as to fix the spinal rod 200 positioned inside the fixing unit 300.

The clamp screw thread 410 is formed at the clamp screw 400 so as to have dents and protrusions with right-angled trapezoidal cross-sections. Thus, when the clamp screw thread 410 engages with the fixing screw thread 310 which is formed in the U-shaped housing groove 330 so as to have the dents and protrusions with the rectangular cross-sections, a predetermined gap is formed between the clamp screw thread 410 and the fixing screw thread 310.

The fixing unit 300 and the clamp screw 400 will now be described in more detail with reference to FIGS. 3 through 6.

Figure 3:
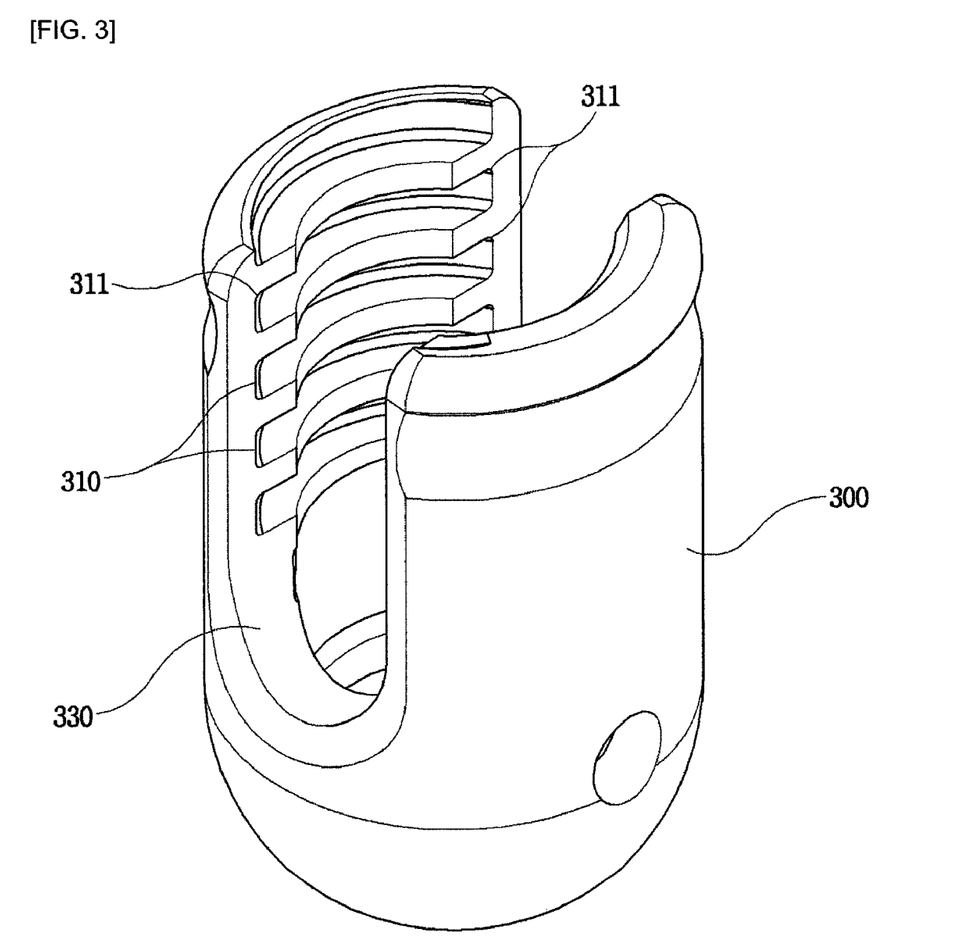
FIG. 3 is a perspective view of a fixing unit of the pedicle screw of FIG. 2.
Figure 4:
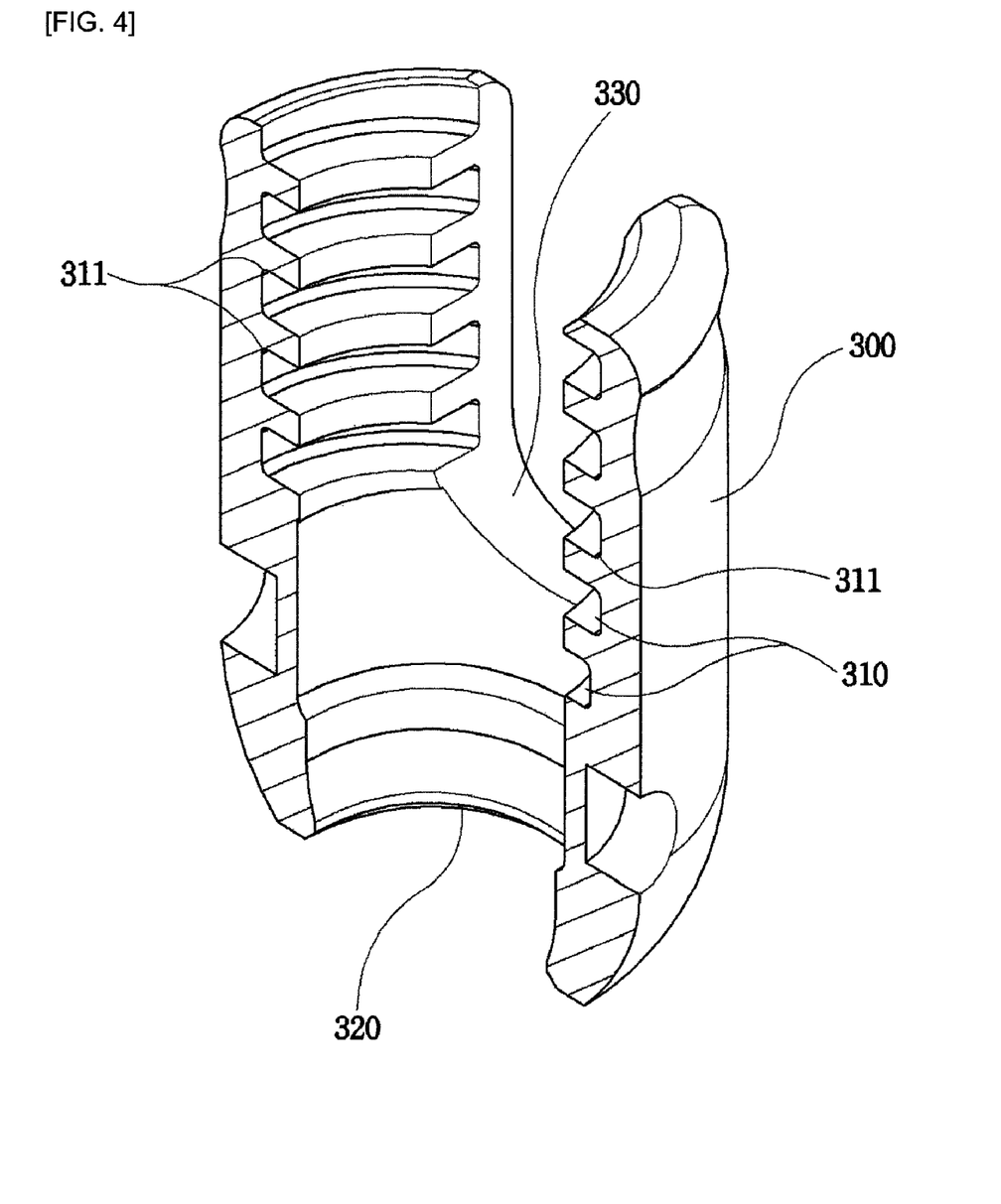
FIG. 4 is a cross-sectional perspective view of the fixing unit of the pedicle screw of FIG. 2.

FIG. 3 is a perspective view of the fixing unit 300 of the pedicle screw of FIG. 2, and FIG. 4 is a cross-sectional perspective view of the fixing unit 300 of the pedicle screw of FIG. 2.

As shown in FIGS. 3 and 4, the fixing unit 300 has a wholly curved cup shape, and includes the U-shaped housing groove 330 which is formed in the side of the fixing unit 300 to be opened upward so as to house the spinal rod 200 and the combination groove 320 which is formed in the lower surface of the fixing unit 300 so as to house the screw bar 100.

The U-shaped housing groove 330 is formed in the same diameter as the spinal rod 200 so that the spinal rod 200 is inserted into the U-shaped housing groove 300 of the fixing unit 300 without separating from the fixing unit 300. The fixing screw thread 310 is formed at the inner surface of the U-shaped housing groove 330 of the fixing unit 300 so as to have the dents and protrusions with the rectangular cross-sections.

The fixing screw thread 310 has the dents and protrusions with the rectangular cross-sections, wherein corners 311 of the dents are rounded. Here, the corners 311 are rounded so as to further firmly combine the fixing screw thread 310 of the fixing unit 300 with the clamp screw thread 410 of the clamp screw 400.

The combination groove 320 of the fixing unit 300 is formed to penetrate the lower surface of the fixing unit 300 so that the screw bar 100 including the spherical joint 110 is inserted into and combined with the fixing unit 300. The screw thread is formed at the inner surface of the combination groove 320 along an inner curvature of the fixing unit 300 so as to engage with and be combined with a screw thread which is formed at an outer surface of the spherical joint 110 of the screw bar 100.

Figure 5:
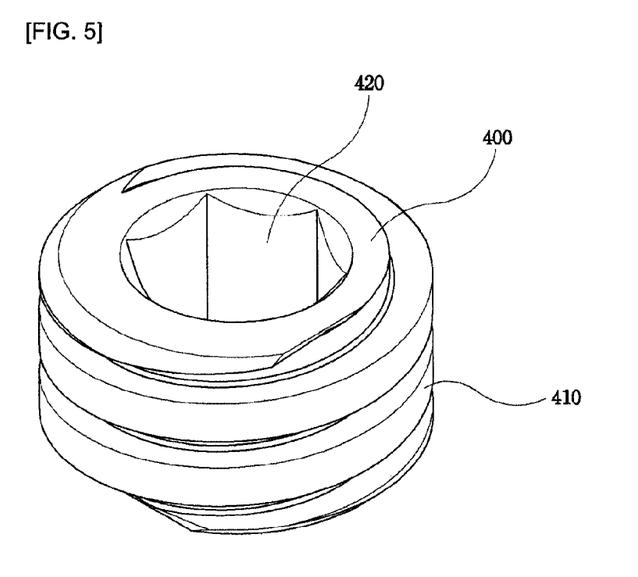
FIG. 5 is a perspective view of a clamp screw of the pedicle screw of FIG. 2.

FIG. 5 is a perspective view of the clamp screw 400 of the pedicle screw of FIG. 2, and FIGS. 6A and 6B are cross-sectional perspective views of the clamp screw 400 of the pedicle screw of FIG. 2.

Figure 6:
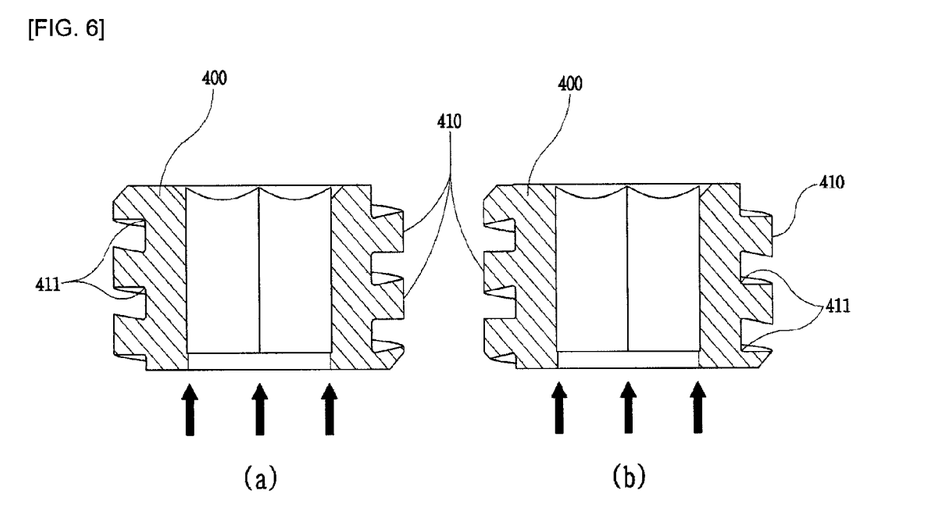
FIGS. 6A and 6B are cross-sectional perspective views of the clamp screw of the pedicle screw of FIG. 2, according to embodiments of the present invention.

As shown in FIGS. 5 and 6, a wrench groove 420 is formed in an upper surface of the clamp screw 400, and the clamp screw thread 410 is formed at the outer surface of the clamp screw 400 so as to be tapered.

The clamp screw thread 410 is formed at the outer surface of the clamp screw 400 so as to have the dents and protrusions with the right-angled trapezoid cross-sections. Here, inclined sides of the right-angled trapezoid protrusions may face upward as shown in FIG. 6A or face downward as shown in FIG. 6B.

The right-angled trapezoid dents of the clamp screw thread 410, i.e., corners 411 of parts which are dented toward a central axis of the clamp screw 400, are rounded like the corners 311 of the dents of the fixing screw thread 310 of the fixing unit 300 described with reference to FIGS. 3 and 4, so as to further easily tighten the clamp screw 400 to the fixing unit 300.

When the fixing screw thread 310 of the fixing unit 300 engages with the clamp screw thread 410 of the clamp screw 400, the right-angled trapezoid protrusions of the clamp screw thread 410 of the clamp screw 400 are inserted into the rectangular dents of the fixing screw thread 310 of the fixing unit 300. Thus, predetermined gaps are formed in the rectangular dents of the fixing screw thread 310.

As shown in FIGS. 6A and 6B, when the spinal rod 200 applies load onto the clamp screw 400 in a direction indicated by arrows, the clamp screw thread 410 of the clamp screw 400 is bent in an opposite direction to the direction due to a strong pressure. Even in this case, a predetermined gap is formed between the fixing screw thread 310 of the fixing unit 300 and the clamp screw thread 410 of the clamp screw 400 so as to prevent the fixing unit 300 from being apart from the clamp screw 400.

In other words, the clamp screw thread 410 is formed so as to form the predetermined gap with the fixing screw thread 310 of the fixing unit 300 without being completely tightened to the fixing screw thread 310 when the clamp screw 400 is combined with the fixing unit 300. Thus, although the clamp screw 400 is deformed by the load applied from the spinal rod 200, the deformation of the clamp screw 400 does not affect the combination between the fixing unit 300 and the clamp screw 400 so as to continuously fix the spinal rod 200 into the fixing unit 300.

Figure 7:
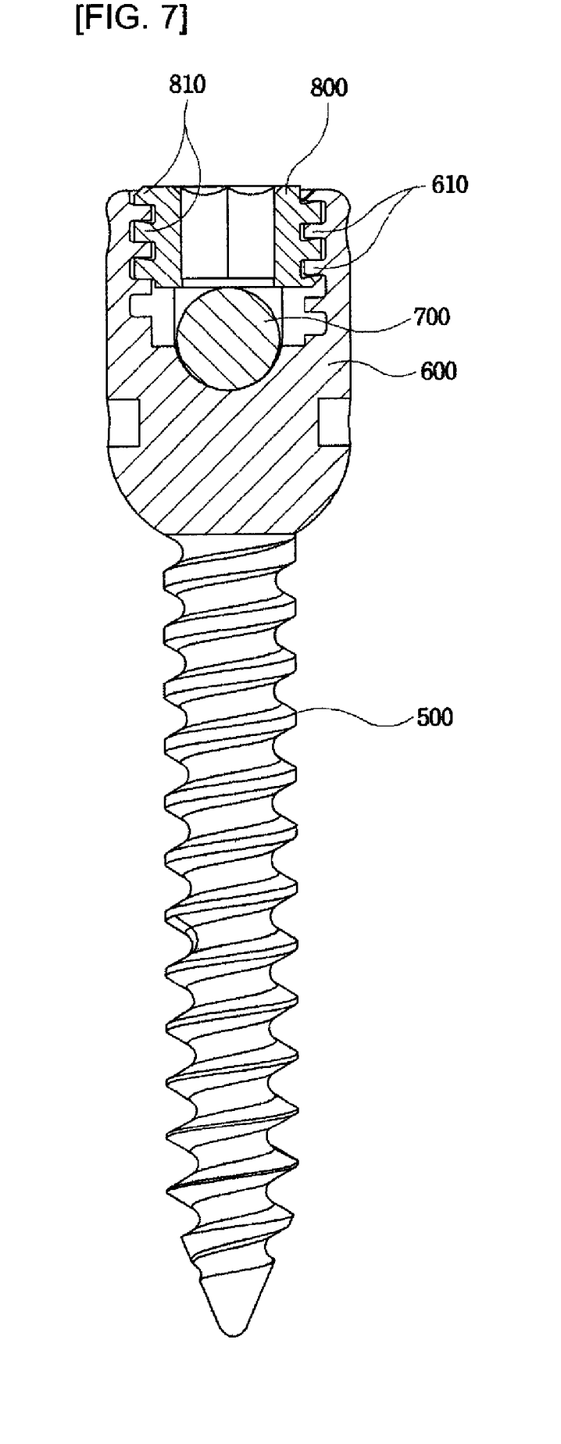
FIG. 7 is a cross-sectional view of a pedicle screw according to another embodiment of the present invention.

FIG. 7 is a cross-sectional view of a pedicle screw according to another embodiment of the present invention. Referring to FIG. 7, the pedicle screw of the present embodiment includes a fixing unit 600 and a screw bar 500 which are combined with each other so as to form a single body. A U-shaped housing groove is formed in the fixing unit 600 so as to house a spinal rod 700.

A fixing screw thread 610 is formed at an inner surface of the U-shaped housing groove to have dents and protrusions with rectangular cross-sections, wherein the dents have rounded corners, so as to engage with and be combined with a clamp screw thread 810 of a clamp screw 800.

The fixing unit 600 and the screw bar 500 of the pedicle screw may be combined with each other so as to form the single body as described above. Alternatively, as described with reference to FIG. 2, the screw bar 500 may be combined with the fixing unit 600 to separate from the fixing unit 600 so as to move inside the fixing unit 600 within a predetermined range. The fixing unit 600 and the screw bar 500 may be combined with each other in various methods besides the above-described methods.

Figure 8:
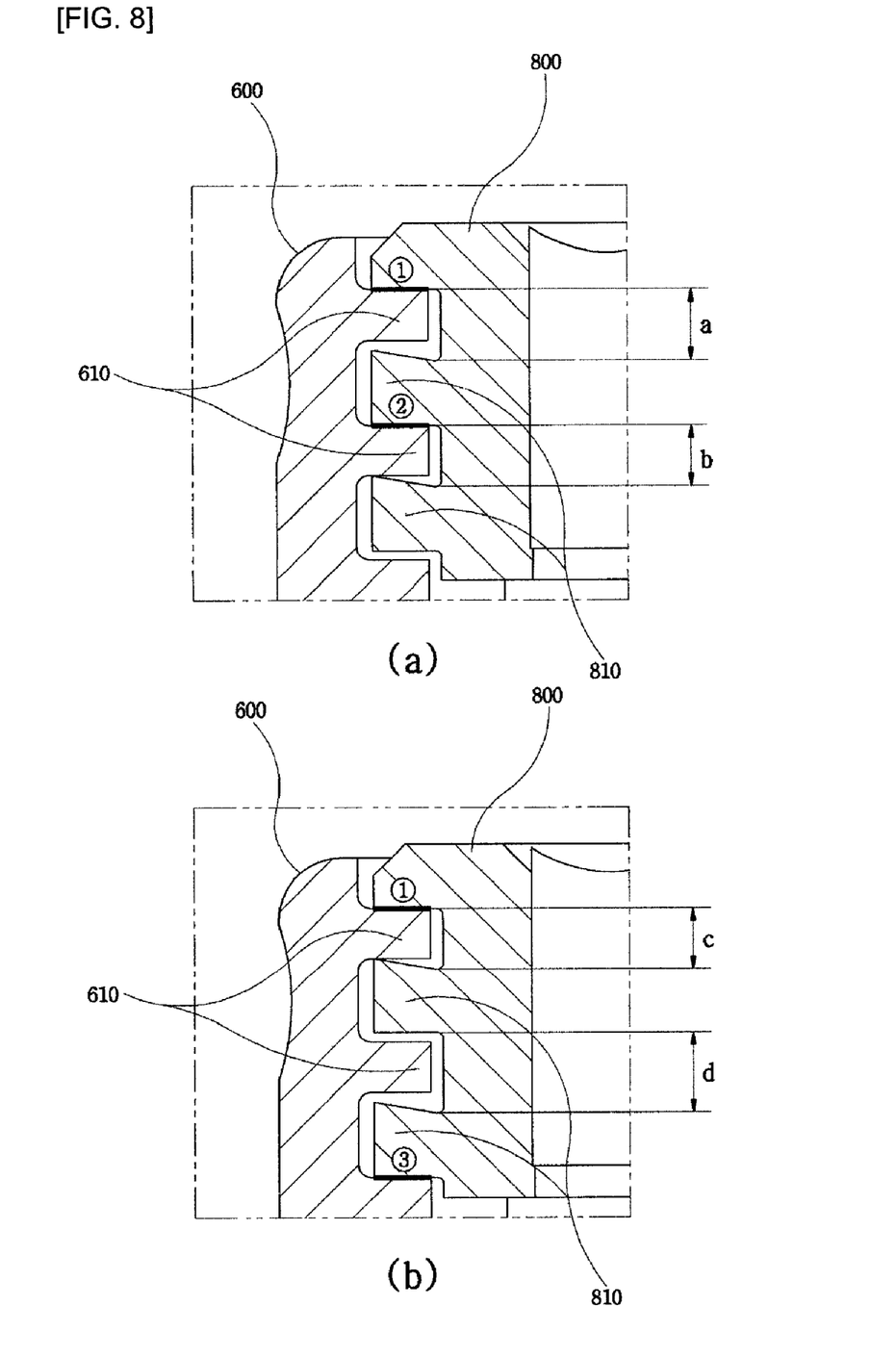
FIGS. 8A and 8B are cross-sectional views of a clamp screw thread of a clamp screw of a pedicle screw, according to embodiments of the present invention.

FIGS. 8A and 8B are cross-sectional views of a clamp screw thread 810 of a clamp screw 800 of a pedicle screw, according to embodiments of the present invention. Referring to FIGS. 8A and 8B, the clamp screw 800 of the pedicle screw according to the present embodiments includes the clamp screw thread 810 which is formed so as to have dents and protrusions with right-angled trapezoid cross-sections. Here, corners of the dents are rounded toward a central axis of the clamp screw 800.

Since the clamp screw thread 810 have different pitches, sides of the clamp screw thread 810 engaged with the fixing screw thread 610 of the fixing unit 600 are different from one another.

As shown in FIGS. 8A and 8B, a lower surface of a protrusion of the clamp screw 810 contacts an upper surface of a protrusion of the fixing screw thread 610 as marked with "①." Also, a lower surface of another protrusion of the clamp screw thread 810 contacts an upper surface of another protrusion of the fixing screw thread 610 as marked with "② or ③" due to the different pitches of the clamp screw thread 810.

Therefore, load applied from a spinal rod is equally dispersed onto upper or lower surfaces of protrusions of the fixing screw thread 610 so as to prevent a neck part of the clamp screw thread 810 from being bent or broken down by the load.

Here, inclined sides of the right-angled trapezoid protrusions of the clamp screw thread 810 face upward as shown in FIGS. 8A and 8B or may face downward.

Distances between the pitches of the clamp screw thread 810 may be reduced downward the clamp screw thread 810 as marked with reference characters "a" and "b" (where "a">"b") of FIG. 8A. The distances between the pitches of the clamp screw thread 810 may be increased downward the clamp screw thread 810 as marked with reference characters "c" and "d" (where "c"<"d") so as to further firmly tighten the clamp screw 800 to the fixing unit 600.

In the pedicle screw according to the present invention as described above, the fixing screw threads 310 and 610 are respectively formed at the inner surfaces of the U-shaped housing grooves of the fixing units 300 and 600 so as to have the dents and protrusions with the rectangular cross-sections, wherein the corners 311 of the dents are rounded. Also, the clamp screw threads 410 and 810 are respectively formed at the outer surfaces of the clamp screws 400 and 800, which are respectively combined with the fixing units 300 and 600, so as to have the dents and protrusions with the right-angled trapezoid cross-sections. Thus, the predetermined gaps are formed between the fixing screw threads 310 and 610 and the clamp screw threads 410 and 810 when the clamp screws 400 and 800 are respectively combined with the fixing units 300 and 600. As a result, although the clamp screws 400 and 800 are bent by the loads applied from the spinal rods 200 and 700, the combinations between the fixing units 300 and 600 and the clamp screws 400 and 800 are prevented from being loosened.

The clamp screw threads 410 and 810 of the clamp screws 400 and 800 have the different pitches so as to disperse the loads which are applied onto the fixing units 300 and 600. As a result, the clamp screws 400 and 800 are further firmly combined with the fixing units 300 and 600 so as to prevent the spinal rods 200 and 700 from being apart from the fixing units 300 and 600.

As described above, a pedicle screw according to the present invention includes a fixing unit which includes a fixing screw thread which is formed at an inner surface of a U-shaped housing groove formed in the fixing unit so as to have dents and protrusions with rectangular cross-sections, wherein corners of the dents are rounded. A clamp screw thread is formed at an outer surface of a clamp screw, which is combined with the fixing unit, so as to have dents and protrusions with right-angled trapezoid cross-sections. Thus, when load is applied onto the clamp screw from a spinal rod, a predetermined gap is formed between the clamp screw thread of the clamp screw and the fixing screw thread of the fixing unit. As a result, although the clamp screw thread of the clamp screw is bent by the load, the clamp screw thread does not push the fixing unit so as to continuously maintain a combination between the clamp screw and the fixing unit.

In addition, pitches of the clamp screw thread of the clamp screw are different from one another so as to equally disperse the load, which is applied from the spinal rod, between the fixing screw thread and the clamp screw thread. Thus, the clamp screw is firmly combined with the fixing unit so as to prevent the spinal rod from being apart from the fixing unit.

While the present invention has been particularly shown and described with reference to exemplary embodiments thereof, it will be understood by those of ordinary skill in the art that various changes in form and details may be made therein without departing from the spirit and scope of the present invention as defined by the following claims.

The embodiments of the invention in which an exclusive property or privilege is claimed are defined as follows:

1. A pedicle screw comprising:
   a fixing unit which comprises a U-shaped housing groove which is formed in a side of the fixing unit to be opened upward so as to house a spinal rod, a fixing screw thread which is formed at an inner surface of the U-shaped housing groove so as to have dents and protrusions with rectangular cross-sections, and a combination groove which is formed in a lower surface of the fixing unit so as to penetrate the lower surface of the fixing unit;

a screw bar which comprises a spherical joint which constitutes an upper part of the screw bar and a screw thread which is formed at an outer surface of the screw bar to be inserted into a pedicle through the combination groove of the fixing unit; and a clamp screw which comprises a clamp screw thread which is formed at an outer surface of the clamp screw to have dents and protrusions with right-angled trapezoid cross-sections so as to form a predetermined gap with the fixing screw thread of the fixing unit when the clamp screw is combined with the fixing unit;

wherein the right-angled trapezoid cross sections of the clamp screw thread decrease in height from a distal end of the right-angled trapezoid cross sections to a proximal end of the right-angled trapezoid cross sections, wherein said proximal end of the right-angled trapezoid cross sections are adjacent the outer surface of the clamp screw.

2. The pedicle screw of claim 1, wherein the fixing screw thread of the fixing unit has the dents and protrusions with the rectangular cross-sections, wherein corners of the dents are rounded.

3. The pedicle screw of claim 1, wherein the clamp screw thread of the clamp screw has the dents and protrusions with the right-angled trapezoid cross-sections, wherein inclined sides of the protrusions of the clamp screw thread face upward or downward, and corners of the dents are rounded toward a central axis of the clamp screw.

4. The pedicle screw of claim 1, wherein pitches of the clamp screw thread are decreased or increased downward the clamp screw thread.

5. A pedicle screw comprising:

a fixing unit which comprises a U-shaped housing groove which is formed in a side of the fixing unit to be opened upward so as to house a spinal rod and a fixing screw thread which is formed at an inner surface of the U-shaped housing groove so as to have dents and protrusions with rectangular cross-sections;

a screw bar which is combined with the fixing unit so as to form a single body with the fixing unit; and a clamp screw which comprises a clamp screw thread which is formed at an outer surface of the clamp screw to have dents and protrusions with right-angled trapezoid cross-sections so as to form a predetermined gap with the fixing screw thread of the fixing unit when the clamp screw is combined with the fixing unit wherein the right-angled trapezoid cross sections of the clamp screw thread decrease in height from a distal end of the right-angled trapezoid cross sections to a proximal end of the right-angled trapezoid cross sections, wherein said proximal end of the right-angled trapezoid cross sections are adjacent the outer surface of the clamp screw.

6. The pedicle screw of claim 5, wherein the fixing screw thread of the fixing unit has the dents and protrusions with the rectangular cross-sections, wherein corners of the dents are rounded.

7. The pedicle screw of claim 5, wherein the clamp screw thread of the clamp screw has the dents and protrusions with the right-angled trapezoid cross-sections, wherein inclined sides of the protrusions of the clamp screw thread face upward or downward, and corners of the dents are rounded toward a central axis of the clamp screw.

8. The pedicle screw of claim 5 wherein pitches of the clamp screw thread are decreased or increased downward the clamp screw thread.

9. The pedicle screw of claim 4, wherein the pitch of the clamp screw thread are decreased or increased from top to bottom such that the clamp screw thread alternates per revolution between engaging an upper protrusion and a lower protrusion of the fixing screw thread.

10. The pedicle screw of claim 8, wherein the pitch of the clamp screw thread are decreased or increased from top to bottom such that the clamp screw thread alternates per revolution between engaging an upper protrusion and a lower protrusion of the fixing screw thread.

* * * * *

UNITED STATES PATENT AND TRADEMARK OFFICE
CERTIFICATE OF CORRECTION

PATENT NO.         : 8,080,036 B2
APPLICATION NO.    : 12/359103
DATED              : December 20, 2011
INVENTOR(S)        : Y. B. Shim et al.

Page 1 of 1

It is certified that error appears in the above-identified patent and that said Letters Patent is hereby corrected as shown below:

In the Claims

| COLUMN | LINE | ERROR |
|---|---|---|
| 8 (Claim 5) | 10 | After "fixing unit" insert --;-- |

Signed and Sealed this
Third Day of September, 2013

Teresa Stanek Rea
*Acting Director of the United States Patent and Trademark Office*